United States Patent [19]

Engle

[11] 4,275,415

[45] Jun. 23, 1981

[54] SCAN CONVERTER

[75] Inventor: Gary L. Engle, Fair Oaks, Calif.

[73] Assignee: Litton Industrial Products, Inc., Beverly Hills, Calif.

[21] Appl. No.: 960,212

[22] Filed: Nov. 13, 1978

[51] Int. Cl.² .............................................. H04N 5/02
[52] U.S. Cl. ................................ 358/140; 343/5 SC; 343/6 TV
[58] Field of Search ........... 358/140; 343/5 SC, 6 TV

[56] References Cited

U.S. PATENT DOCUMENTS

| | | | |
|---|---|---|---|
| 3,765,018 | 10/1973 | Heard | 343/5 SC |
| 4,002,827 | 1/1977 | Nevin | 358/140 |
| 4,149,252 | 4/1979 | Miller | 358/140 |

Primary Examiner—Howard W. Britton

Attorney, Agent, or Firm—Robert A. Seldon

[57] ABSTRACT

A scan converter, used in an imaging system, for inverting the R-$\theta$ format of stored data into a format compatible with video display. As the video display is scanned horizontally, the $\theta$ addresses are sequentially addressed by means responsive to the scan position. The switch points thus defined are updated within succeeding video lines in accordance with trigonometric relationships between the video lines and the radial lines. Means responsive to the scanning of a reference video line initializes the switch point values in accordance with respective intersection points of the displayed radial lines and the reference video line.

The R coordinate is similarly initialized and updated in accordance with trigonometric relationships between the radial lines and the video lines.

5 Claims, 5 Drawing Figures

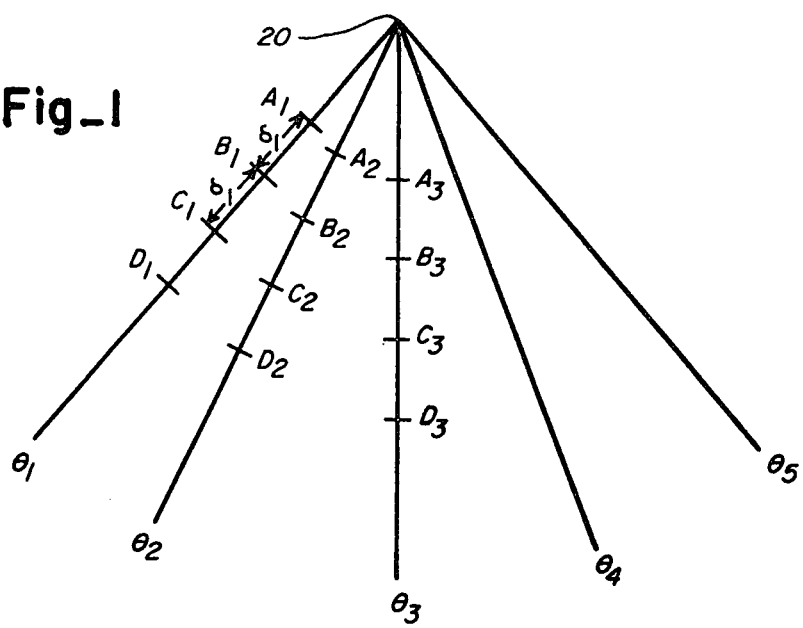
Fig_1
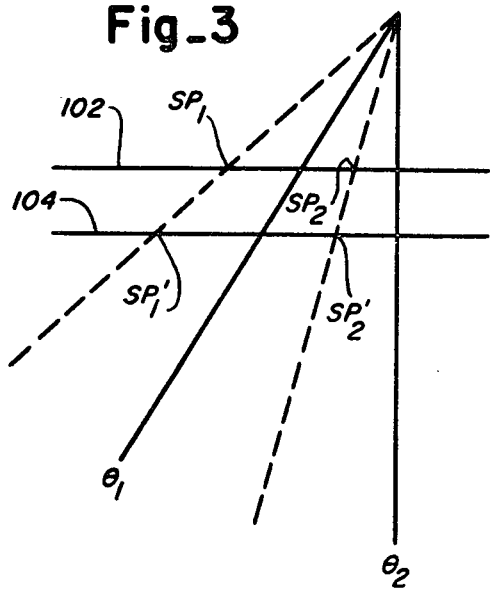
Fig_2
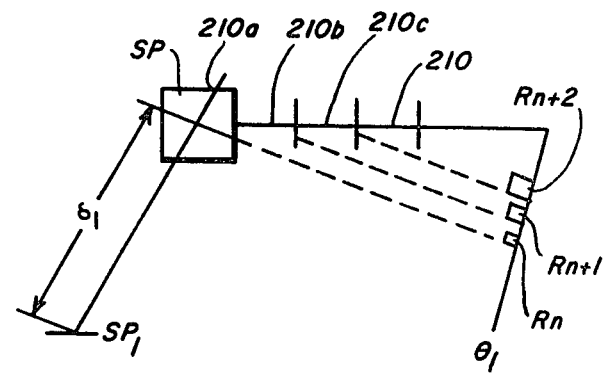
Fig_3
Fig_4

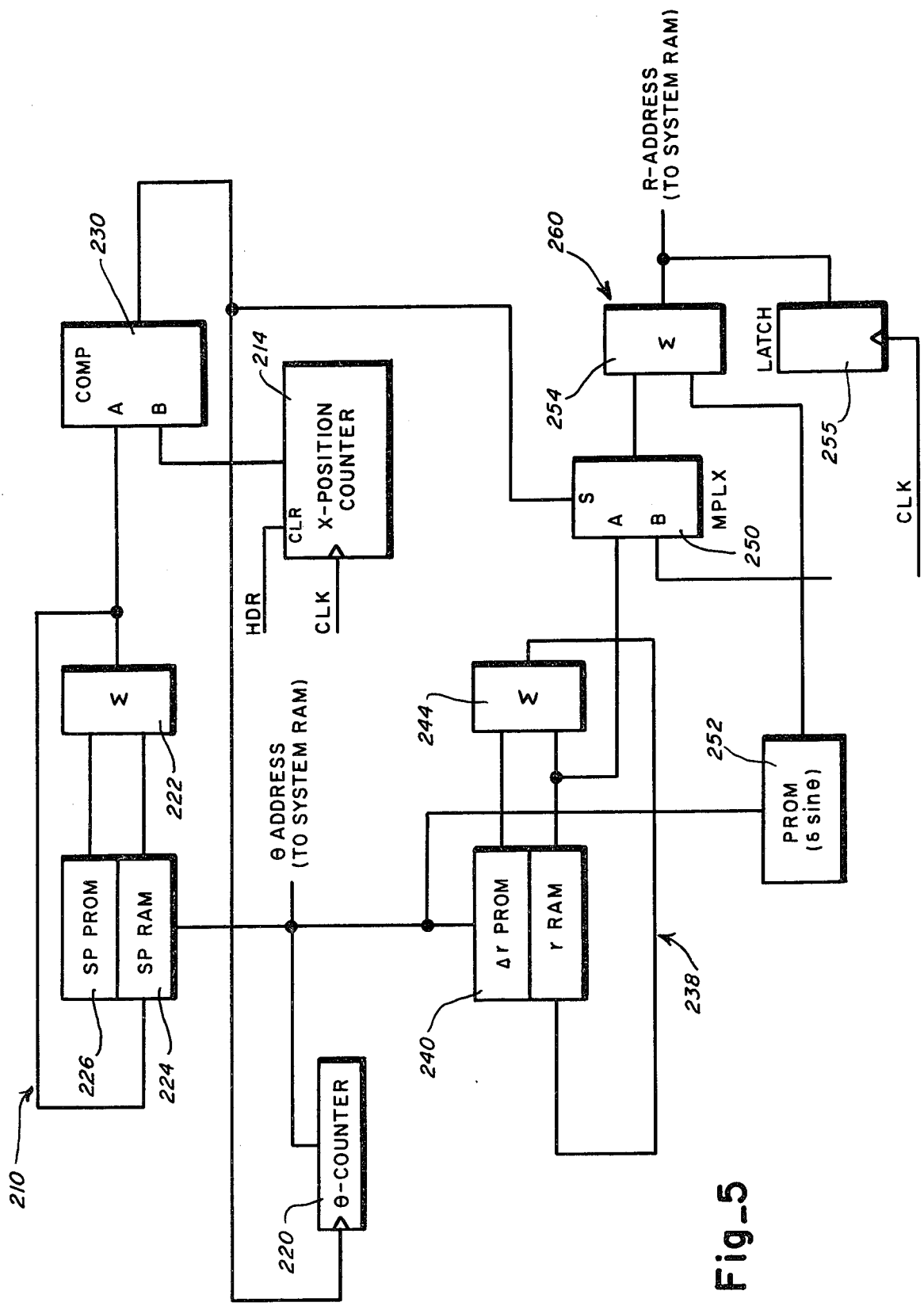
Fig_5

SCAN CONVERTER

FIELD OF THE INVENTION

This invention relates to imaging systems wherein the amplitudes and return times of reflections generated by discontinuities in the propagation path of an energy pulse, provide the data necessary to construct an image of the path-defining media. The invention is more particularly concerned with that portion of the system, known as the scan converter, which converts the format of the incoming data into one which is compatible with the display scan.

Video monitors are preferable to x-ray CRT displays for three major reasons. First, video display permits a gray scale so that reflection amplitudes may be visually represented as gray levels rather than brightness levels so that perception of the display is not effected by ambient lighting or by reflection weakness. Secondly, video taping is preferable to film for record keeping since such tapes can be reused and the recording/playback equipment is relatively inexpensive. Thirdly, video displays readily lend themselves to the use of remote monitors so that the displays may be observed in several locations.

Generally, the format of the incoming data is on a path-by-path basis, with the reflection amplitude at particular return times for each path being stored prior to the launching of a pulse along the next path. The data must be arranged for access by the display, which is preferably a video monitor having a video beam which scans a matrix of video picture elements in an interlaced raster pattern. The data must accordingly be available on a video line-by-line basis and in the proper sequential order as the beam moves along each line.

In some imaging systems, propagation paths are generally radial, extending from either an actual or projected origin region. This configuration may result when the location of the pulse-generating transducer changes along a generally circular path about the examined body, owing either to transducer movement or to the use of a transducer array. This configuration is particularly useful in the medical field for cardiac imaging systems, where a phased curved array surrounding the chest cavity may be conveniently used to focus between the ribs.

SUMMARY OF THE PRIOR ART

Conventionally, images formed by radial sectors have been first produced on x-y monitors and then transferred to video format by a video camera monitoring the x-y display. Besides losing the gray scale information and a degree of brightness, the approach is undesirable owing to hardware cost.

It is therefore a goal of the present invention to provide a video image of a sector without the need for an intermediate x-y monitor. It is additionally intended to provide a technique which is compatible with real time imaging.

SUMMARY OF THE INVENTION

The present invention is, accordingly, a scan converter which is adapted to directly read out the data in stored R-$\theta$ coordinates in a format compatible with video display. Generally, the trigonometric relationships between the imaged radially-extending propagation paths and the video lines are utilized to correctly address the image system memory. As the video display is scanned horizontally, the $\theta$ coordinate is successively incremented as successive switch points are scanned by the display. The switch points are initialized in accordance with the intersection of respective radial lines with the reference video line. The switch points are then incremented in accordance with the trigonometric relationships between succeeding video lines and the respective radial lines. Similarly, the R coordinate is initialized during the scan of a reference video line and incremented in accordance with the incremental length of each radial line between the successive video lines.

The scan converter, and its utilized technique, may be more readily appreciated by reference to the description of the preferred embodiment, set forth below, which is to be read in conjunction with the following drawings.

BRIEF DESCRIPTION OF THE DRAWINGS

In the drawings:

FIG. 1 is an illustrative depiction of a plurality of generally radially-extending pulse propagation paths, FIG. 2 illustratively depicts the memory surface of a scan converter adapted to store the data associated with the propagation paths of FIG. 1 in an R-$\theta$ coordinate format, FIG. 3 illustratively depicts the relationship between a pair of the displayed radial paths, and a pair of successive video lines, FIG. 4 illustrates a portion of the video line which diplays data derived from a particular radial path, and FIG. 5 is a block diagram schematic representation of a scan converter constructed in accordance with the present invention.

DESCRIPTION OF THE PREFERRED EMBODIMENT

FIG. 1 illustratively depicts a plurality of pulse propagation paths $\theta$, $-\theta_5$. The paths are seen to extend from a common point 20 which may be the focal point of a phased array of transducers or of a curved transducer array. In operation a pulse is launched along a path $\theta_1$, and sufficient time allowed to receive the reflection from discontinuities in the propogation path before a pulse is launched along path $\theta_2$, etc. Naturally, one or more additional pulses may be launched along a path before proceeding to the next path. A series of data points A–D are thereby defined on each path and represent regions for which data, in the form of reflection amplitudes, has been taken.

The points A–D may be derived by sampling the incoming data at a succession of equally spaced time intervals so that the regions along each path are equally spaced from each other. In addition, the time intervals may be the same for each path so that corresponding points of each path are at similar distances from the origin O; in other words $OA_1 = OA_2 = OA_3$, $OB_1 = OB_2 = OB_3$, etc. Alternatively, the sample rate may vary from path to path. For each region A–D, the sampled data is indicative of the amplitudes of respective reflections and may, of course, be "0" if no reflection is present at the sampling time.

FIG. 2 illustratively depicts the memory surface of the scan converter. The memory 30 is shown to comprise a plurality of data-storage locations respectively associated with a radial distance R along a particular path $\theta$. Each location may accordingly be addressed by coordinates R, $\theta$ and sampled data may be written into memory be systematically incrementing the "R" address while addressing the $\theta$ locations associated with the particular path being monitered.

The technique by which data stored in the R-$\theta$ format may be directly displayed on a video screen, which employs the standard raster pattern, most easily explained by initial reference to FIG. 3. In FIG. 3, a video display including a pair of essentially horizontal video lines 102, 104 is illustratively shown. The displayed position of two radial lines $\theta_2$ and $\theta_3$ is superimposed. It will be appreciated that only data for regions A–D will be displayed, leaving gaps between radial lines $\theta$ as well as between regions on each radial line.

In practice, the gaps between radial lines is much smaller than the exaggerated spacing illustrated for clarity. Preferably, with a 64 line pattern, the radials are approximately $1\frac{1}{2}°$ apart and, for a conventional video display of $512 \times 512$ picture elements (pixels), the gaps have a maximum width of 8 pixels. To preclude such gaps, the data is typically "smeared"; that is, the data for each particular region is used from surrounding regions to fill in the gaps.

For illustration, it will be assumed that video line 102 represents the first line of the image area and that video line 104 is the first video line requiring new data; i.e. data has been "smeared" between lines 102 and 104. As the video beam scans horizontally along line 102, it will reach a position $SP_1$ at which data from radial line $\theta_1$ is to be used. The data from radial line $\theta_1$ will be used for display until a second position $SP_2$ is reached and data from radial line $\theta_2$ is used. The data associated with the other radial lines are similarly accessed as the beam continues its horizontal scan.

There are several "smearing" techniques possible in addition to the preferred method hereinafter described. One technique would entail the accessing of the $\theta_1$ value at the intersection of the $\theta_1$ line and video line 102. That $\theta_1$ value would be used to modulate the video beam between points $SP_1$ and $SP_2$. However, the resulting "horizontal smearing" creates distortions which are less preferable than that of the "tangential smearings" conveniently provided by the present invention.

As shown in FIG. 4, tangential smearing may be provided by finding the radial distance R along the radial line $\theta$ at which the radial line is intersected by a perpendicular line dropped from the horizontal position of the video beam and subsequently reading the data associated with the sector line $\theta$ at the radial distance R. Thus, the data associated with radial region $R_{\theta1,1}$ is used to modulate the video beam as $SP_1$ while the values $R_{\theta1,2}$, $R_{\theta1,3}$, etc. are used at successive horizontally scanned pixels 210, 220, etc.

The actual distance along the radial line $\theta_1$ of each region $R_{\theta,n}$ may be calculated from the previous $R_{\theta,n-1}$ by the trigonometric identity (1) $R_{\theta,n} = R_{\theta,n-1} - \delta \sin \theta$, where $\delta$ is the distance between horizontal video lines.

It will be evident to one skilled in the art that data from appropriate points on the $\theta_1$ line will be used until a second horizontal position $SP_1^\theta 2$ is reached, whereupon the foregoing technique is repeated.

At the end of the horizontal video line 102, the video beam retraces to the start of line 104 and is blanked until reaching the position $SP_2^\theta 1$. While the position may be identified in a number of ways, use may be made of the trigometric relationship between $SP_1^\theta 1$ and $SP_\theta^\theta 1$, namely $$SP_2 = SP_1^\theta 1 - \frac{\delta}{\tan(\theta_1 - E)} \quad (2)$$

and the similar relationship between the horizontal starting positions associated with each radial line. This as hereinafter described lends itself to the use of a "scratchpad" memory arrangement in which only a limited amount of successively incremented positional information need be carried forward during the scan.

FIG. 5 is a block diagram schematic representation of a scan converter constructed in accordance with the present invention for producing the R and $\theta$ addresses required by the data-storing memory of the imaging system. The $\theta$ coordinate of the R-$\theta$ address is provided by a counter 220. For the preferred line density of 64 radial lines, the $\theta$ counter 220 requires 6 bytes. In addition to addressing the image system RAM, the $\theta$ counter 220 also addresses programmable read-only memories (PROMs) 225, 240, 252. The purpose of the PROMs will become apparent from the following description of the circuit.

Specifically, the circuitry depicted in FIG. 5 operates as the video beam is scanning horizontally to repeatedly determine when the next succeeding radial line $\theta_{i+1}$ is to be the data source and, further, to identify the position of the data, R, within the data set associated with the accessed radial line.

In the preferred embodiment, the data associated with the next successive radial line $\theta_{i+1}$ is accessed when the video beam is within a predetermined distance of the radial line: preferably midway between the lines $\theta_i$ and $\theta_{i+1}$. Previously noted, the switch point SP which is obtained from the radial line $\theta_{i+1}$ rather than $\theta_i$ may be based on the corresponding switch point for the previous video line in accordance with equation 2 above. As shown in the illustration, switch point circuitry 210 computes the horizontal switch point $SP_\theta$ for each radial line and compares the actual horizontal video beam position with the calculated upcoming switch point and increments the $\theta$-counter 220 when the switch point position is reached.

The circuitry 210 is shown to include an SP PROM 226 and an SP RAM 224 coupled to respective inputs of a summer 222. The output of the summer 222 is coupled to one input of a comparator 230 and also to the input of the SP RAM 224. The SP RAM comprises a $4 \times 64$ memory which is addressed by the $\theta$ counter 220 to store respective values of SP for each of the 64 radial lines. The SP PROM functions to store the increment $\delta/10(\theta)$ for each of the 64 radial lines. It will be apparent to those skilled in the art that the data in the SP RAM 224 locations will be successively updated in accordance with the increment stored in the SP PROM 225 as the $\theta$ counter 220 is incremented from $\theta_1$ to $\theta_{64}$ in accordance with equation 2 above to provide the switch point values.

Input A of the comparator accordingly represents the horizontal video beam position at which $\theta$ should be read from the next radial line. Coupled to the other input of the comparator 230 is an x-position counter 214 which is reset with the horizontal retrace HDR of the video display and clocked with a system clock of approximately 10 MHc. When the horizontal video beam position becomes equal to the computed switch position SP, the comparator output increments the $\theta$ counter 220. It may be seen that the $\theta$ counter 220 is incremented through all the θ addresses with every video line and may be reset with the horizontal drive signal HDR. At the commencement of a video line, the SP RAM is addressed for the value $\theta_1$ switch point at the previous video line and the SP PROM 225 is addressed to provide the correct value of the increment. At the next horizontally displaced position of the video beam, the comparator 230 operates to increment the θ counter 220 which, in turn, addresses the next location in the SP RAM 224 to obtain the switch point SP for the next successive radial line $\theta_2$ and a new increment from the SP PROM 225 is derived.

Having explained the manner by which data sets associated with respective radial lines θ are determined, attention is next directed to the manner in which the correct data (r) within the data set is selected. As indicated previously, it is desirable to select different data values as the video beam progresses horizontally in order to provide tangential smearing of the stored data. Thus, effectively, data will be read as different radial distances along the same radial line θ as the video beam scans horizontally between the successive switch points SP (FIG. 3).

The circuitry for determining the radial distance associated with each horizontal beam position is indicated generally at 238 and operates in a similar manner to the circuitry 210 discussed immediately above. The circuitry 238 operates to produce an output at the summer 244 in accordance with equation 1 above so that the r PROM 240 contains 64 values respectively associated with the radial lines θ and having a value equal to $\delta/\sin(\theta + E)$.

The tangential smearing circuitry, generally indicated at 260, provides the R coordinate of the R-θ address to the imaging system RAS. The circuitry 240 includes a summer 254 having a pair of inputs respectively coupled to a PROM 252 and a multiplexer 250. The PROM 252 is addressed by the θ counter 220, as previously indicated, and stores respective incremental values of sin θ for each of the radial lines. It will be appreciated that, with the selection of input B by the multiplexer 250, the operation of the circuit 240 will be similar to circuits 210 and 238 so that the R coordinate to the image system RAM will be constantly changed in conformance with equation 1 above; namely, $R_{i+1} = R_i - \sin\theta_i$. The starting value of R for the next successive radial line $\theta_{i+1}$ is accordingly selected by the multiplexer when the θ-counter 220 changes. The output of the r PROM is subtracted from the present r at every system clock pulse. As explained earlier, the system clock pulses correspond to horizontal crossing of pixel boundaries by the video beam. When the θ counter 220 is updated, the multiplexer is consequently switched to the new r which is thereafter used and the new increment subtracted therefrom.

While the foregoing detailed description is of a preferred embodiment of the present invention, it will be understood that many variations and modifications by those skilled in the art are possible. It is intended that all these variations and modifications be included within the scope of the following appended claims.

I claim:

1. In an imaging system of the type wherein a plurality of energy pulses are launched along respective generally radial paths in a region to be examined and reflections from discontinuities in the paths are received, the system being of the type including video display means including a matrix of video picture elements and means for scanning successive lines of the matrix, and a system memory having addressable locations for storing input data in an R-θ format wherein the R co-ordinate is indicative of elapsed time between a pulse launching and reflection sampling and wherein the θ co-ordinate is indicative of the particular radial path sampled, a scan converter for accessing the system memory locations in a sequence compatible with the scan pattern of the video display means, the scan converter comprising:

θ-co-ordinate address means responsive to respective trigger signals to sequentially address the data sets of the radial lines;

first memory means responsive to the θ-co-ordinate address means for storing switch point values indicative of the respective scan positions of the video scan means along a video line at which the data sets of a respective successive radial line is to be addressed;

means responsive to the scanning of a reference video line for initializing the switch point values in accordance with respective intersection positions of the displayed radial lines and the reference video line;

second memory means responsive to the θ-co-ordinate address means for producing first increment values respectively indicative of the changes in displayed intersection positions of the radial lines with succeeding video lines;

first summing means for updating the switch point values in accordance with the respective increments subsequent to the scanning of the switch point position;

third memory means responsive to the θ-co-ordinate address means for producing values related to respective radial distances along the radial lines;

means responsive to the scanning of a reference video line for initializing the radial distance values in accordance with the distance from the origin of the radial paths to the paths intersections with the reference video line;

fourth memory means responsive to the θ-co-ordinate address means for producing second increment values respectively indicative of radial length changes in the displayed intersection positions of the radial line with succeeding video lines;

second summing means for updating the radial distance values in accordance with respective increment values subsequent to the scanning of a respective switch point; and comparator means for producing the trigger signal indicative of the crossing of a switch point by the video scan means.

2. The scan converter of claim 1 including means for displaying input data in the display regions between successive radial lines.

3. The scan converter of claim 2 including means for obtaining data for each picture element in the gap from the accessed radial line data set at a radial distance generally corresponding to the intersection of a generally perpendicular line from the picture element to the accessed radial line.

4. The scan converter of claim 3 including fifth memory means responsive to the θ-coordinate address means for producing third incremental values respectively indicative of radial length changes in the radial lines for successive video lines, third means responsive to the scanning of successive picture elements between switch points for summing the radial distance values in the third memory means with respective third incremental values to produce a signal value corresponding to an adjusted R-address coordinate.

5. The scan converter of claim 4 including multiplex means responsive to the trigger signal to produce a selected one of the accessed distance values in the fourth memory means and an adjusted distance value, the third summing means for summing the selected signal and the addressed third increment value to produce the adjusted distance value as the R address coordinate to the system memory.

* * * * *